United States Patent [19]

Fischer et al.

[11] 4,115,641
[45] Sep. 19, 1978

[54] RIBOFURANOSYL-IMIDAZOLE DERIVATIVES

[75] Inventors: Ulf Fischer, Frenkendorf; Pierre-Charles Wyss, Muttenz, both of Switzerland

[73] Assignee: Hoffmann-La Roche Inc., Nutley, N.J.

[21] Appl. No.: 820,501

[22] Filed: Aug. 1, 1977

[30] Foreign Application Priority Data

Aug. 6, 1976 [AT] Austria ................................ 5859/76

[51] Int. Cl.² ............................................. C07H 17/00
[52] U.S. Cl. ........................................ 536/23; 424/180
[58] Field of Search ........................................ 536/23

[56] References Cited

U.S. PATENT DOCUMENTS

| 3,832,341 | 8/1974 | Duschinsky | 526/24 |
| 3,855,205 | 12/1974 | Prasad | 536/24 |
| 3,864,483 | 6/1973 | Stein | 536/24 |
| 3,897,415 | 7/1975 | Robin et al. | 536/23 |

FOREIGN PATENT DOCUMENTS

| 130,685 | 3/1975 | Denmark | 536/24 |
| 7,125,625 | 6/1972 | France | 536/24 |
| 2,105,560 | 9/1972 | Fed. Rep. of Germany | 536/24 |
| 2,160,104 | 3/1973 | Fed. Rep. of Germany | 536/24 |
| 2,342,479 | 3/1975 | Fed. Rep. of Germany | 536/23 |
| 7,109,584 | 1/1972 | Netherlands | 536/24 |
| 7,602,711 | 3/1976 | Netherlands | 536/24 |

Primary Examiner—Johnnie R. Brown
Assistant Examiner—Blondel Hazel
Attorney, Agent, or Firm—Samuel L. Welt; George M. Gould; William G. Isgro

[57] ABSTRACT

Ribofuranoysl-imidazole derivatives of the formula

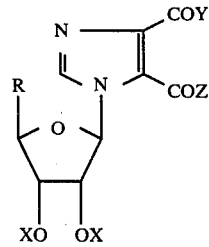

wherein R, X, Y and Z have one of the meanings set forth hereinafter, are described. The ribofuranosyl-imidazole derivatives have cardiac and circulatory-dynamic properties and are useful in the treatment of angina pectoris.

17 Claims, No Drawings

RIBOFURANOSYL-IMIDAZOLE DERIVATIVES

BRIEF SUMMARY OF THE INVENTION

Ribofuranosyl-imidazole derivatives of the formula

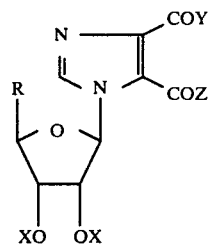

wherein R, X, Y and Z have one of the meanings set forth hereinafter under (1)–(5):
(1) R is —CH$_2$OH;
X is H; and
Y and Z are —C$_{1-4}$-alkoxy, —NH(C$_{1-7}$-alkyl), —NH(-C$_{2-4}$-alkenyl), —NH(C$_{3-6}$-cycloalkyl) or —NH-aralkyl; or
(2) R is —CH$_2$ONO$_2$;
X is —NO$_2$; and
Y and Z are —C$_{1-4}$-alkoxy, —NH$_2$, —NH(C$_{1-7}$-alkyl), —NH(C$_{2-4}$-alkenyl), —NH-(aralkyl) or —N(NO$_2$)(-C$_{1-7}$-alkyl); or
(3) R is —COO(C$_{1-4}$-alkyl), —CONH$_2$, —CONH(C$_{1-4}$-alkyl), —CONH(C$_{2-4}$-alkenyl); —CONH(C$_{3-6}$-cycloalkyl) or —CO—Het (Het meaning a nitrogen-containing heterocyclic ring bound to the carbonyl group via a nitrogen atom);
X is H; and
Y and Z are —NH$_2$ or —NH(C$_{1-7}$-alkyl); or
(4) R is —COO(C$_{1-4}$-alkyl);
X is —NO$_2$; and
one of Y and Z is —NH$_2$ and the other is —NHNO$_2$; or
(5) R is —CONH$_2$, —CONH(C$_{1-4}$-alkyl) or —CONH(-C$_{5-6}$-cycloalkyl);
X is —NO$_2$; and
both of Y and Z are —NH$_2$, —NH(C$_{1-7}$-alkyl) or —N(-NO$_2$)(C$_{1-7}$-alkyl) or one of Y and Z is —NH$_2$ and the other is —NHNO$_2$,
as well as a process for the manufacture thereof are described. The ribofuranosylimidazole derivatives of the invention have cardiac and circulatory-dynamic properties, and are useful in the treatment of angina pectoris.

DETAILED DESCRIPTION OF THE INVENTION

The invention relates to imidazole derivatives. More particularly, the invention is concerned with ribofuranosyl-imidazole derivatives, a process for the preparation thereof and pharmaceutical dosage forms containing same.

The ribofuranosyl-imidazole derivatives of the invention are compounds of the formula

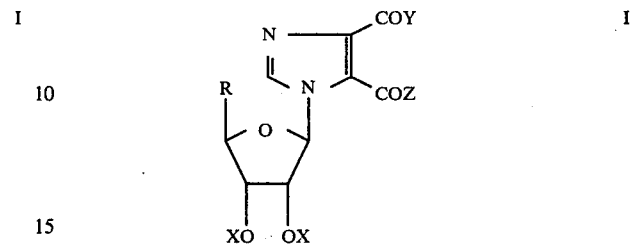

wherein R, X, Y and Z have one of the meanings set forth hereinafter under (1)–(5):
(1) R is —CH$_2$OH;
X is H; and
Y and Z are —C$_{1-4}$-alkoxy, —NH(C$_{1-7}$-alkyl), —NH(-C$_{2-4}$-alkenyl), —NH(C$_{3-6}$-cycloalkyl) or —NH-aralkyl; or
(2) R is —CH$_2$ONO$_2$;
X is —NO$_2$; and
Y and Z are —C$_{1-4}$-alkoxy, —NH$_2$, —NH(C$_{1-7}$-alkyl), —NH(C$_{2-4}$-alkenyl), —NH-(aralkyl) or —N(NO$_2$)(-C$_{1-7}$-alkyl); or
(3) R is —COO(C$_{1-4}$-alkyl), —CONH$_2$, —CONH(C$_{1-4}$-alkyl), —CONH(C$_{2-4}$-alkenyl), —CONH(C$_{3-6}$-cycloalkyl) or —CO-Het (Het meaning a nitrogen-containing heterocyclic ring bound to the carbonyl group via a nitrogen atom);
X is H; and
Y and Z are —NH$_2$ or —NH(C$_{1-7}$-alkyl); or
(4) R is —COO(C$_{1-4}$-alkyl);
X is —NO$_2$; and
one of Y and Z is —NH$_2$ and the other is —NHNO$_2$; or
(5) R is —CONH$_2$, —CONH(C$_{1-4}$-alkyl) or —CONH(-C$_{5-6}$-cycloalkyl);
X is —NO$_2$; and
both of Y and Z are —NH$_2$, —NH(C$_{1-7}$-alkyl) or —N(-NO$_2$) (C$_{1-7}$-alkyl) or one of Y and Z is —NH$_2$ and the other is —NHNO$_2$.

The groups of compounds defined hereinbefore under (1) to (5) correspond, in the specification, to the following formulas:
I-1 (with the sub-groups I-11 and I-12);
I-2 (with the sub-groups I-21 and I-22 and I-23);
I-3 (with the sub-groups I-31 and I-32);
I-4; and
I-5 (with the sub-groups I-51 and I-52).

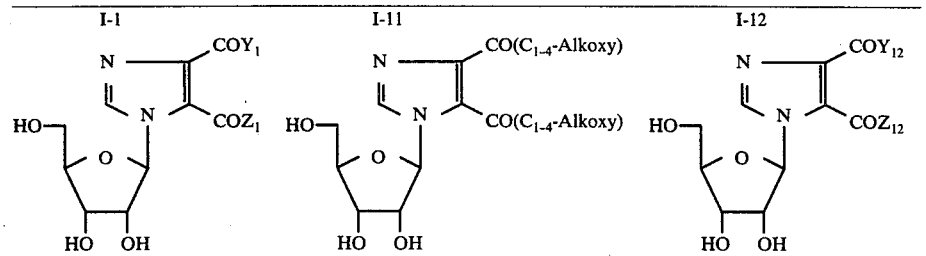

wherein Y$_1$ and Z$_1$ are:
—C$_{1-4}$-alkoxy
—NH(C$_{1-7}$-alkyl)

wherein Y$_{12}$ and Z$_{12}$ are:
—NH(C$_{1-7}$-alkyl)

-continued

| | |
|---|---|
| —NH(C_{2-4}-alkenyl)<br>—NH(C_{3-6}-cycloalkyl)<br>—NH-alkaryl | —NH(C_{2-4}-alkenyl)<br>—NH(C_{3-6}-cycloalkyl)<br>—NH-alkaryl |

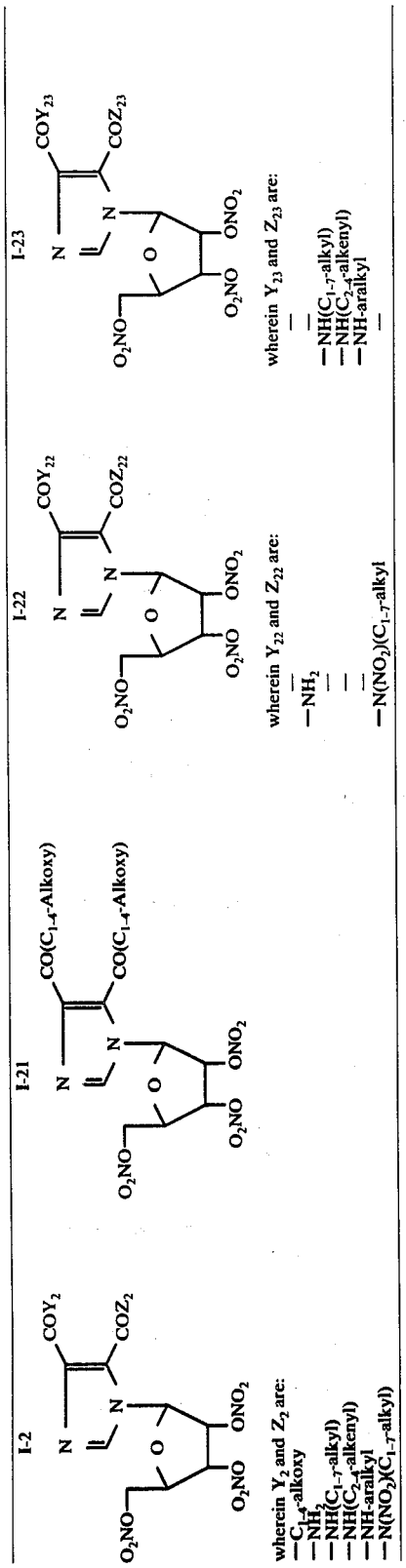

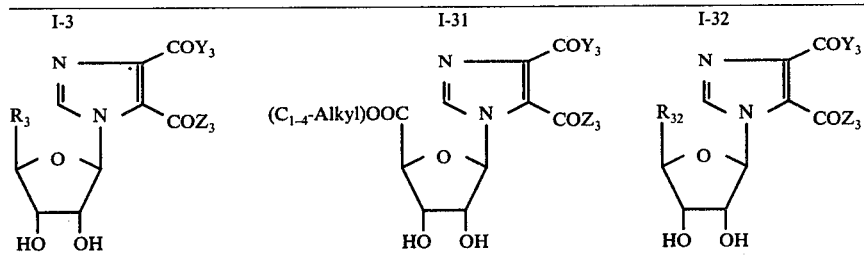

wherein R₃ is:
—COO($C_{1-4}$-alkyl)
—$CONH_2$
—CONH($C_{1-4}$-alkyl)
—CONH($C_{2-4}$-alkenyl)
—CONH($C_{3-6}$-cycloalkyl)
—CO-Het and $Y_3$ and $Z_3$ are:
—$NH_2$
—NH($C_{1-7}$-alkyl)

wherein $R_{32}$ is:
—$CONH_2$
—CONH($C_{1-4}$-alkyl)
—CONH($C_{2-4}$-alkenyl)
—CONH($C_{3-6}$-cycloalkyl)
—CO-Het

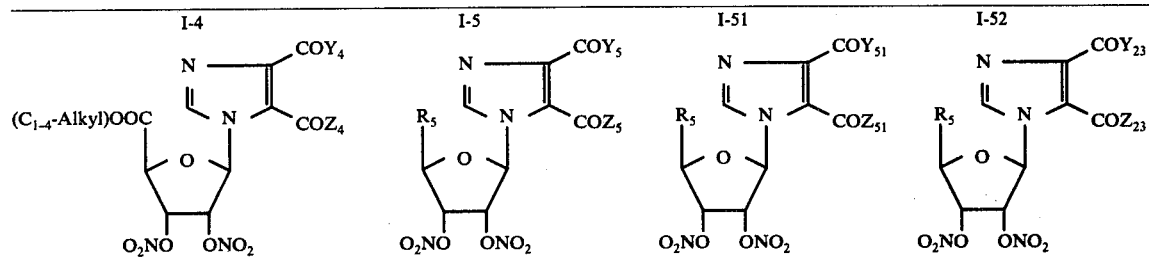

wherein one of $Y_4$ and $Z_4$ is: —$NH_2$ and the other is —$NHNO_2$ wherein $R_5$ is:
—$CONH_2$
—CONH($C_{1-4}$-alkyl)
—CONH($C_{5-6}$-cycloalkyl)
and $Y_5$ and $Z_5$ both are:
—$NH_2$
—NH($C_{1-7}$-alkyl)
—N($NO_2$)($C_{1-7}$-alkyl)
or one of $Y_5$ and $Z_5$ is —$NH_2$ and the other is —$NHNO_2$ wherein $Y_{51}$ and $Z_{51}$ both are:
—$NH_2$,
—N($NO_2$)($C_{1-7}$-alkyl)
or one of $Y_{51}$ and $Z_{51}$ is —$NH_2$ and the other is —$NHNO_2$ wherein $Y_{23}$ and $Z_{23}$ are:
—NH($C_{1-7}$-alkyl)
—NH($C_{2-4}$-alkenyl)
—NH-aralkyl According to the process provided by the present invention, the compounds of formula I hereinbefore can be prepared as follows:

1. To prepare compounds of formula I-11, cleaving the T-protecting groups from a compound of the formula

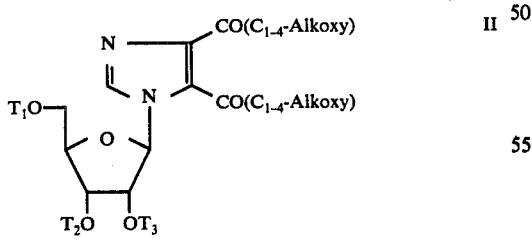

wherein $OT_1$, $OT_2$ and $OT_3$ each independently are a protected hydroxyl group;

2. To prepare compounds of formula I-21, nitrating a compound of formula I-11;

3. To prepare compounds of formula I-12, subjecting a compound of formula I-11 or a compound of formula II, wherein $T_1$, $T_2$ and $T_3$ each are an acyl group, to treatment with an amine of the formula $HY_{12}$, wherein $Y_{12}$ has the meaning given earlier;

4. To prepare compounds of formula I-22, nitrating a compound of the formula

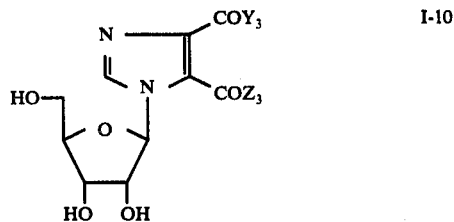

where $Y_3$ and $Z_3$ are as previously described;

5. To prepare compounds of formula I-23, subjecting a compound of the formula

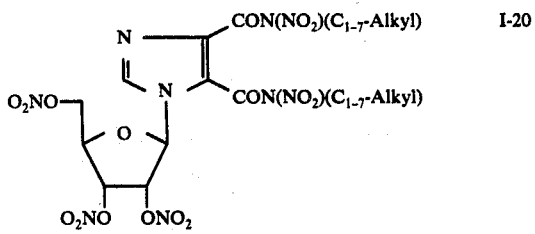

to aminolysis with an amine of the formula $HY_{23}$, wherein $Y_{23}$ is as previously described;

6. To prepare compounds of formula I-31, esterifying the carboxyl group present in a compound of the formula

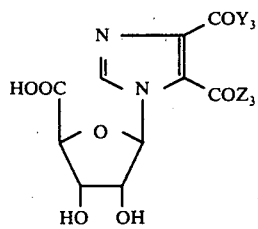

III wherein $Y_3$ and $Z_3$ are as previously described, with an agent providing a ($C_{1-4}$-alkyl) group;

7. To prepare compounds of formula I-32, treating a compound of formula I-31 with $NH_3$ or an amine of the formula ($C_{1-4}$-alkyl)$NH_2$, ($C_{2-4}$-alkenyl)$NH_2$, ($C_{3-6}$-cycloalkyl)$NH_2$ or H-Het;

8. To prepare compounds of formula I-4, nitrating a compound of the formula

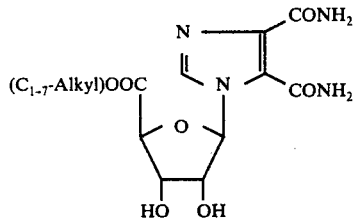

I-30

9. To prepare compounds of formula I-51, nitrating a compound of the formula

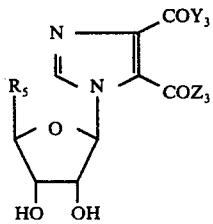

I-321 wherein $R_5$, $Y_3$ and $Z_3$ are as previously described;

10. To prepare compounds of formula I-52, treating a compound of the formula

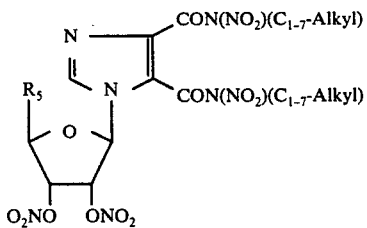

I-511 wherein $R_5$ is as previously described, with an amine of the formula $HY_{23}$, wherein $Y_{23}$ is as previously described.

The protected hydroxyl groups present in the starting materials of formula II are of the conventional type. Examples of T-protecting groups are those which are readily removable by hydrolysis or by catalytic hydrogenation, for example, "acyl" groups, for instance, an "alkanoyl" group derived from an aliphatic carboxylic acid of 1 to 7 carbon atoms, such as formyl, acetyl, or the like, and an "aroyl" group derived from an aromatic carboxylic acid, such as benzoyl. Such T-protecting groups also include benzyl or alkylidene groups. Thus, for example, $T_2$ and $T_3$ together can be the isopropylidene group.

The terms "alkyl" and "alkenyl" as used herein denote a straight-chain and branched-chain alkyl and alkenyl group, respectively, which contain the stated number of carbon atoms, examples of alkyl groups are methyl, ethyl, propyl, isopropyl, n-butyl, isobutyl, tert.butyl, and the like, and examples of alkenyl groups are allyl, methallyl, and the like. The heterocyclic rings denoted by "Het" are preferably 5-membered or 6-membered heterocyclic rings which may contain, in addition to the nitrogen atom via which they are bound with the carbonyl group, other hetero atoms, for example, nitrogen, oxygen or sulfur. Exemplary of such heterocyclic rings are pyrrolidino, piperidino, morpholino, and the like. The term "aralkyl" includes, in particular, a phenyl-(lower alkyl) group, such as benzyl or phenethyl. The groups Y and Z are generally, but not necessarily, identical. Insofar as no identity exists, this is expressly stated.

The previously referred-to process embodiments 1-10 are more precisely described hereinafter:

1. Preparation of the compounds of formula I-11

The cleavage of the T-protecting groups from the starting materials of formula II can be carried out according to known methods. For example, benzoyl protecting groups can be cleaved by treatment with catalytic amounts of an alkali alkanolate, such as sodium methylate in methanol, conveniently at room temperature.

2. Preparation of the compounds of formula I-21

The nitration of the compounds of formula I-11 can be carried out in a known manner using nitric acid, if desired, in the presence of oleum, conveniently at a low temperature, preferably a temperature in the range of from $-30°$ C. to $-10°$ C.

3. Preparation of the compounds of formula I-12

The conversion of an ester of formula I-11 into an amide of formula I-12 can be carried out according to known methods of aminolysis by treating an ester of formula I-11 with an amine of the formula $HY_{12}$. The esters of formula I-11, which can be obtained as described earlier starting from compounds of formula II by cleavage of the protecting groups, need not be isolated prior to the aminolysis, but can be subjected to in situ aminolysis. Also, for example, a compound of formula II wherein $T_1$, $T_2$ and $T_3$ each are acyl can be treated with an amine of the formula $HY_{12}$, this treatment brings about not only cleavage of the acyl protecting groups but also aminolysis of the ester function in one operation.

4. Preparation of compounds of formula I-22

The nitration of the compounds of formula I-10 can be carried out under analogous conditions as described earlier for the conversion of compounds of formula I-11 into compounds of formula I-21. When a compound of formula I-10 wherein $Y_3$ and $Z_3$ both are —NH($C_{1-7}$-alkyl) is utilized, then not only the hydroxyl groups but also the amide groups are nitrated with the formation of compounds of formula I-22 wherein both $Y_{22}$ and $Z_{22}$ are $-N(NO_2)(C_{1-7}\text{-alkyl})$.

5. Preparation of compounds of formula I-23

The aminolysis of compounds of formula I-20 can be carried out according to known methods by treatment with an amine of the formula $HY_{23}$, conveniently in an inert solvent, preferably an alkanol or an ether, such as tetrahydrofuran, at room temperature.

6. Preparation of compounds of formula I-31

The esterification of the carboxyl group present in the compounds of formula III can be carried out in a known manner, for example, by treating a compound of formula III with diazomethane to provide the methyl ester or with a $C_{1-4}$-alkanol in the presence of p-toluenesulfonic acid or thionyl chloride.

The compounds of formula III can be prepared from the compounds of formula I-10, for example, by protecting the secondary hydroxyl groups of a compound of formula I-10, conveniently by ketalization, oxidizing the hydroxymethyl group to the carboxyl group, for example, utilizing potassium permanganate or chromium trioxide, and finally liberating the secondary hydroxyl groups. The compounds of formula III are preferably prepared by the catalytic oxidation of the compounds of formula I-10.

7. Preparation of compounds of formula I-32

The conversion of an ester of formula I-31 into an amide of formula I-32 can be carried out in a known manner by treating an ester of formula I-31 with ammonia or an amine of the formula $(C_{1-4}\text{-alkyl})NH_2$, $(C_{2-4}\text{-alkenyl})NH_2$, $(C_{3-6}\text{-cycloalkyl})NH_2$ or H—Het.

8. Preparation of compounds of formula I-4

The nitration of the compounds of formula I-30 can be carried out under analogous conditions as described earlier for the nitration of compounds of formula I-10. One of the amide groups, either that in the 4-position or that in the 5-position, is thereby nitrated.

9. Preparation of compounds of formula I-51

The nitration of compounds of formula I-321 can also be carried out under the conditions described earlier for the preparation of compounds of formula I-21.

10. Preparation of compounds of formula I-52

The aminolysis of compounds of formula I-511 can be carried out under analogous conditions to those described earlier for the conversion of compounds of formula I-20 into compounds of formula I-23.

The compounds provided by the invention possess valuable effects on the heart, such as coronary dilating effects, and on the circulatory-dynamics and can, accordingly, be used as medicaments, inter alia, for the treatment of angina pectoris. Dosages in the amount of 0.01–30 mg/kg body weight per day can be utilized. Such a dosage can be administered not only as a single dose but preferably several times daily in divided doses.

The compounds provided by the invention can be used as pharmaceutical preparations, having direct or delayed release of the active ingredient, which contain them in association with a compatible pharmaceutical carrier material. Such carrier material can be an organic or inorganic inert carrier material suitable for enteral, percutaneous or parenteral administration, such as, for example, water, gelatin, gum arabic, lactose, starch, magnesium stearate, talc, vegetable oils, polyalkyleneglycols, or the like. The pharmaceutical preparations can be made up in a solid form, for example, as tablets, dragees, suppositories or capsules, in semi-solid form, for example, as salves or in liquid form, for example, as solutions, suspensions or emulsions. The pharmaceutical preparations may be sterilized and/or may contain adjuvants such as preservatives, stabilizers, wetting agents, emulsifiers, flavor-improving agents, salts for varying the osmotic pressure or buffer substances. The pharmaceutical preparations can be prepared in a known manner.

The starting materials used in the foregoing process are known or can be prepared according to known methods or in analogy to the methods described in the Examples hereinafter.

The coronary dilating activity can be measured and demonstrated according to the following method:

Mongrel dogs weighing between 20 and 35 kg. are used in the experiment. The dogs are narcotized with 35 mg/kg. i.v. of pentobarbital, intubated tracheally and artifically respirated with room air. After opening the thorax, the heart is exposed and a previously calibrated flow probe of an electro-magnetic flowmeter is placed around the Ramus circumflexus of the left coronary artery to measure the amount of blood flowing through. The arterial blood pressure is measured with a pressure transducer via a catheter in the Aorta ascendens. The pulse wave triggers a tachograph for measurement of the heart frequency. For the investigation of possible adenosine-like and nitroglycerine-like modes of action, a coronary segment analysis is carried out according to Winbury (Winbury, M. et al., J. Pharmacol. Exp. Ther. 168 (1), 70–95, 1969). The compounds to be tested are administered intravenously dissolved in propyleneglycol. The maximum activity of a compound is calculated for each dosage in percent of the starting value and the duration of action is determined in each case.

The pharmacological data obtained for several compounds provided by the present invention are compiled in the following Table:

Table

| Compound of formula I wherein: | n | Dose i.v. [mg/kg] | BP Δ % [min] | HR Δ % [min] | CABF Δ % [min] | Type of activity |
|---|---|---|---|---|---|---|
| A  R = CH$_2$OH, X = H   Y = Z = —NHCH$_3$ | 2 | 1.0 | −14  5 | −6  20 | +146  20 | A |
| B  R = CH$_2$ONO$_2$, X = —NO$_2$   Y = Z = —NHCH$_3$ | 2 | 0.03 | −42  60 | 0 | −29  60 | N |
| C  R = —CONH$_2$, X = H   Y = Z = —NH$_2$ | 2 | 1.0 | −3  5 | 0 | +74  30 | A |
| D  R = —CONH$_2$, X = —NO$_2$ | | | | | | |

Table-continued

| Compound of formula I wherein: | n | Dose i.v. [mg/kg] | BP Δ % [min] | HR Δ % [min] | CABF Δ % [min] | Type of activity |
|---|---|---|---|---|---|---|
| Y = Z = —NH$_2$ | 2 | 1.0 | —40  60 | +10  5 | —20  60 | N | n = Number of animals
BP = Arterial blood pressure
HR = Heart rate
CABF = Coronary flow
A = Adenosine-like
N = Nitroglycerine-like The following Examples further illustrate the invention. All temperatures are in degrees Centigrade, unless otherwise mentioned.

EXAMPLE 1

Preparation of dimethyl 1-β-D-ribofuranosyl-imidazole-4,5-dicarboxylate

A solution of 5 g. of dimethyl 1-(2,3,5-tri-O-benzoyl-β-D-ribofuranosyl)-imidazole-4,5-dicarboxylate and 50 mg. of sodium methylate in 100 ml. of methanol is left to stand at room temperature for 1 hour. The solution is then neutralized with glacial acetic acid and evaporated to dryness. The residue is chromatographed over silica gel with a mixture of chloroform and ethanol. Recrystallization from methanol/isopropyl ether gives 1.3 g. of dimethyl 1-β-D-ribofuranosyl-imidazole-4,5-dicarboxylate, having a melting point of 125° C. (decomposition).

The tribenzoyl derivative used as the starting material can be prepared as follows:

(a) A suspension of 6 g. of dimethyl imidazole-4,5-dicarboxylate in 30 ml. of hexamethyldisilazane and 0.5 ml. of trimethylchlorosilane is boiled under reflux for 2 days. The solution obtained is evaporated to dryness and the residue distilled at 150° C./0.08 Torr. 7.8 G. of dimethyl 1-(trimethylsilyl)-imidazole-4,5-dicarboxylate are obtained.

Diethyl 1-(trimethylsilyl)-imidazole-4,5-dicarboxylate can be prepared in an analogous manner.

(b) 101 G. of 1-O-acetyl-2,3,5-tri-O-benzoyl-β-D-ribofuranose and 51.3 g. of dimethyl 1-(trimethylsilyl)-imidazole-4,5-dicarboxylate are dissolved in 1 liter of ethylene chloride. A solution of 23.6 ml. of tin tetrachloride in 500 ml. of ethylene chloride is then added dropwise while stirring and cooling with ice. After the dropwise addition, the mixture is left to stand at room temperature for 2 days. The solution is diluted with 1 liter of methylene chloride and poured while stirring into 1.5 liters of a saturated sodium hydrogen carbonate solution. The mixture is stirred for a further 1 hour and then filtered. The phases are separated and the aqueous phase is extracted with 250 ml. of methylene chloride. The organic phase is dried over sodium sulfate and evaporated. The residue is chromatographed over silica gel with a mixture of hexane and ethyl acetate. After recrystallization from methanol/petroleum ether, there are obtained 98.1 g. of dimethyl 1-(2,3,5-tri-O-benzoyl-β-D-ribofuranosyl)-imidazole-4,5-dicarboxylate, having a melting point of 123°–124° C.

Diethyl 1-(2,3,5-tri-O-benzoyl-β-D-ribofuranosyl)-imidazole-4,5-dicarboxylate, $[α]_D^{25}$ = 3.5° (c = 1.00 in chloroform) can be prepared in an analogous manner by reacting diethyl 1-(trimethylsilyl)-imidazole-4,5-dicarboxylate with 1-O-acetyl-2,3,5-tri-O-benzoyl-β-D-ribofuranose.

The tribenzoyl derivative used as the starting material can also be prepared as follows:

A mixture of 27.7 g. of 1-O-acetyl-2,3,5-tri-O-benzoyl-β-D-ribofuranose and 9.2 g. of dimethyl imidazole-4,5-dicarboxylate is melted in an oil-bath which is held at a temperature of 200° C. 200 Mg. of bis-(p-nitrophenyl)-phosphate are then added and the heating to 200° C. while stirring and under reduced pressure is continued for 30 minutes. The mixture is chromatographed over silica gel with a mixture of hexane and ethyl acetate. Recrystallization from methanol/petroleum ether gives 13.1 g. of product which is identical with the product obtained in accordance with paragraph (b) earlier.

The tribenzoyl derivative used as the starting material can also be prepared as follows:

A solution of 15.2 g. of 2,3,5-tri-O-benzoyl-D-ribofuranosyl chloride and 8.1 g. of dimethyl 1-(trimethylsilyl)-imidazole-4,5-dicarboxylate in 100 ml. of methylene chloride is left to stand at room temperature for 18 hours. The mixture is filtered and the filtrate washed with a saturated sodium hydrogen carbonate solution and water. The methylene chloride solution is dried over sodium sulfate and evaporated. The residue is chromatographed over silica gel with a mixture of hexane and ethyl acetate. After recrystallization from methanol/petroleum ether, there is obtained 0.9 g. of product which is identical with the product obtained in accordance with paragraph (b) earlier.

EXAMPLE 2

Preparation of N,N'-dimethyl-1-β-D-ribofuranosyl-imidazole-4,5-dicarboxamide

A suspension of 30 g. of dimethyl 1-(2,3,5-tri-O-benzoyl-β-D-ribofuranosyl)-imidazole-4,5-dicarboxylate in 400 ml. of 40% aqueous methylamine solution is stirred at room temperature. After 18 hours, the clear solution is evaporated to dryness and the residue evaporated twice with 100 ml. of water each time. The residue is digested in 100 ml. of water and the mixture left to stand overnight in a refrigerator. The product is then filtered off and washed with water. After recrystallization from isopropanol, there are obtained 13.6 g. of N,N'-dimethyl-1-β-D-ribofuranosyl-imidazole-4,5-dicarboxamide, having a melting point of 193° C.

The following compounds are manufactured in an analogous manner by reacting dimethyl 1-(2,3,5-tri-O-benzoyl-β-D-ribofuranosyl)-imidazole-4,5-dicarboxylate with the corresponding amines:

N,N'-bis-(2-methylallyl)-1-β-D-ribofuranosyl-imidazole-4,5-dicarboxamide of melting point 157° C.;

N,N'-diallyl-1-β-D-ribofuranosyl-imidazole-4,5-dicarboxamide of melting point 160° C.;

N,N'-dicyclopropyl-β-D-ribofuranosyl-imidazole-4,5-dicarboxamide of melting point 205°–206° C.;

N,N'-diethyl-1β-D-ribofuranosyl-imidazole-4,5-dicarboxamide of melting point 172°–174° C.

EXAMPLE 3

Preparation of
N,N'-diphenethyl-1-β-D-ribofuranosyl-imidazole-4,5-dicarboxamide

A solution of 26.4 g. of diethyl 1-(2,3,5-tri-O-benzoyl-β-D-ribofuranosyl)-imidazole-4,5-dicarboxylate in 500 ml. of methanol is treated with 49 g. of phenethylamine and the mixture left to stand at room temperature for 3 days. The mixture is then evaporated to dryness. The residue is digested in 100 ml. of methanol, and the mixture left to stand overnight in a refrigerator. The product is filtered off, washed with methanol and recrystallized from methanol. There are obtained 17.2 g. of N,N'-diphenethyl-1-β-D-ribofuranosyl-imidazole-4,5-dicarboxamide, having a melting point of 148° C.

The following compounds are manufactured in an analogous manner by reacting diethyl 1-(2,3,5-tri-O-benzoyl-β-D-ribofuranosyl)-imidazole-4,5-dicarboxylate with the corresponding amines:

N,N'-diheptyl-1β-D-ribofuranosyl-imidazole-4,5-dicarboxamide of melting point 88°-90° C.;

N,N'-dipropyl-1-β-D-ribofuranosyl-imidazole-4,5-dicarboxamide of melting point 163° C.

EXAMPLE 4

Preparation of methyl
1-desoxy-1-(4,5-dicarbamoylimidazol-1-yl)-β-D-ribofuranuronate A suspension of 16.2 g. of 1-desoxy-(4,5-dicarbamoyl-imidazol-1-yl)-β-D-ribofuranuronic acid in 2.6 litres of methanol is treated with an ethereal diazomethane solution until the solution obtained retains a light yellow color. The solution is then evaproated to dryness and the residue recrystallized from methanol. These are obtained 14.9 g. of methyl 1-desoxy-1-(4,5-dicarbamoylimidazol-1-yl)-β-D-ribofuranuronate, having a melting point of 203°-204° C. (decomposition).

The ribofuranuronic acid used as the starting material can be prepared as follows:

(a) 20 g. of 1-β-D-ribofuranosyl-imidazole-4,5-dicarboxamide [see, for example, J. Chem. Soc. 1949, 232] are dissolved in 2 litres of water at 80° C. Platinum (obtained by hydrogenating 10 g. of platinum oxide) is added. Oxygen is blown into the suspension with vigorous stirring. The temperature is held at 80° C. 8.6 G. of sodium hydrogen carbonate are added in several portions so that the mixture always remains alkaline. After 2 days, the catalyst is filtered off, the filtrate concentrated to 100 ml. and acidified with trifluoroacetic acid while cooling with ice-water. The crystallizing solution is left to stand overnight in a refrigerator and the product is then filtered off. 12.4 G. of 1-desoxy-1-(4,5-dicarbamoylimidazol-1-yl)-β-D-ribofuranuronic acid are obtained.

The ribofuranuronic acid used as the starting material can also be prepared as follows:

(b) A suspension of 54.7 g. of 1-β-D-ribofuranosyl-imidazole-4,5-dicarboxamide in 1.4 litres of acetone and 100 ml. of acetone dimethylacetal is treated with 13.6 g. of p-toluenesulfonic acid monohydrate and the mixture stirred at room temperature for 2 days. The mixture is then filtered and the filtrate evaporated to dryness. The residue is taken up in 1 litre of water, neutralized with sodium hydrogen carbonate and extracted with ethyl acetate. The ethyl acetate extract is dried over sodium sulfate and concentrated. The crystallizing solution is left to stand overnight in a refrigerator and the product then filtered off. After recrystallization from ethyl acetate, there are obtained 45.1 g. of 1-(2,3-O-isopropylidene-β-D-ribofuranosyl)-imidazole-4,5-dicarboxamide, having a melting point of 151°-153° C.

15.9 G. of 1-(2,3-O-isopropylidene-β-D-ribofuranosyl)-imidazole-4,5-dicarboxamide are dissolved in 1.5 liters of water and the solution is treated with 5.5 g. of potassium hydroxide and thereafter with 23.2 g. of potassium permanganate. After 2 hours, the mixture is filtered, excess potassium permanganate in the filtrate decomposed with 30% hydrogen peroxide, again filtered and the filtrate concentrated to 250 ml. This solution is acidified with trifluoroacetic acid while cooling with ice-water. The crystallizing product is left to stand overnight in a refrigerator and filtered off. After recrystallization from ethanol, there are obtained 7.8 g. of 1-desoxy-1-(4,5-dicarbamoylimidazol-1-yl)-2,3-O-isopropylidene-β-D-ribofuranuronic acid, having a melting point greater than 250° C.

1 G. of 1-(2,3-O-isopropylidene-β-D-ribofuranosyl)-imidazole-4,5-dicarboxamide is treated in 10 ml. of glacial acetic acid with 0.4 g. of chromium trioxide and the mixture is stirred at room temperature. After 36 hours, the precipitated product is filtered off and washed with glacial acetic acid and diethyl ether. 0.4 G. of 1-desoxy-1-(4,5-dicarbamoylimidazol-1-yl)-2,3-O-isopropylidene-β-D-ribofuranuronic acid is obtained.

A suspension of 20.2 g. of 1-desoxy-1-(4,5-dicarbamoyl-imidazol-1-yl)-2,3-O-isopropylidene-β-D-ribofuranuronic acid in 500 ml. of trifluoroacetic acid and 120 ml. of water is stirred at room temperature. After 30 minutes, the clear solution is evaporated to dryness and the residue evaporated twice with 100 ml. of water each time. The residue is digested in 50 ml. of water and the mixture left to stand overnight in a refrigerator. The product is then filtered off and washed with water. There are obtained 16.7 g. of product which is identical with the product obtained in accordance with paragraph (a) earlier in this Example.

EXAMPLE 5

Preparation of methyl
1-[4,5-bis-(ethylcarbamoyl)-imidazol-1-yl]-1-desoxy-β-D-ribofuranuronate 14.5 G. of platinum dioxide are suspended in 1000 ml. of water and hydrogenated to platinum After the addition of 7.4 g. of potassium hydrogen carbonate and 21.75 g. of N,N'-diethyl-1-β-D-ribofuranosyl-imidazole-4,5-dicarboxamide, the mixture is warmed to 75° C. and oxygen is blown in for 6 hours while stirring. After filtration of the platinum, the solution is evaporated almost to dryness and the residue acidified while cooling by the addition of 75 ml. of 1-N hydrochloric acid. Thereby, these precipitate 23.6 g. of free acid which is suspended in methanol without further purification and converted into its methyl ester by treatment with ethereal diazomethane solution until a yellow color remains.

Recrystallization from ethyl acetate/petroleum ether gives 13.5 g. of methyl 1-[4,5-bis-(ethylcarbamoyl)-imidazol-1-yl]-1-desoxy-β-D-ribofuranuronate, having a melting point of 142°-144° C.

EXAMPLE 6

Preparation of methyl
1-desoxy-1-(4,5-dicarbamoylimidazol-1-yl)-β-D-ribofuranuronate 7.4 G. of 1-desoxy-1-(4,5-dicarbamoylimidazol-1-yl)-β-D-ribofuranuronic acid and 4 g. of p-toluenesulfonic acid are boiled at reflux in 1.5 litres of methanol for 4 hours. The solution obtained is cooled down to room temperature and concentrated, crystals separating out. The crystallizing solution is left to stand overnight in a refrigerator. The reaction product is then filtered off and recrystallized from methanol. There are obtained 3.2 g. of methyl 1-desoxy-1-(4,5-dicarbamoylimidazol-1-yl)-β-D-ribofuranuronate which is identical with the product obtained according to Example 4.

EXAMPLE 7

Preparation of ethyl
1-desoxy-1-(4,5-dicarbamoylimidazol-1-yl)-β-D-ribofuranuronate A suspension of 16.8 g. of 1-desoxy-(4,5-dicarbamoylimidazol-1-yl)-β-D-ribofuranuronic acid in 1.7 liters of ethanol is treated with 17 ml. of thionyl chloride at 0° to 5° C. and the mixture stirred at room temperature for 18 hours. The solution obtained is neutralized with pyridine and evaporated to dryness. The residue is digested in 200 ml. of ethanol and filtered off. After recrystallization from ethanol, there are obtained 9.3 g. of ethyl 1-desoxy-1-(4,5-dicarbamoylimidazol-1-yl)-β-D-ribofuranuronate, having a melting point of 212°–213° C (decomposition).

EXAMPLE 8

Preparation of
1-(β-D-ribofuranuronamidosyl)-imidazole-4,5-dicarboxamide

A solution of 4.2 g. of methyl 1-desoxy-1-(4,5-dicarbamoylimidazol-1-yl)-β-D-ribofuranuronate in 250 ml. of methanol, which has been saturated at 0° C. with anhydrous ammonia, is left to stand at room temperature for 3 days in a closed pressure flask. The mixture is then evaporated to dryness and the residue recrystallized from methanol/water. There are obtained 3.8 g. of 1-(β-D-ribofuranuronamidosyl)-imidazole-4,5-dicarboxamide, having a melting point of 244°–245° C. (decomposition).

EXAMPLE 9

Preparation of
1-(N-methyl-β-D-ribofuranuronamidosyl)-imidazole-4,5-dicarboxamide a suspension of 1.5 g. of methyl 1-desoxy-1-(4,5-dicarbamoylimidazol-1-yl)-β-D-ribofuranuronate in 100 ml. of methanol is treated with 25 ml. of 40% methylamine and the mixture stirred at room temperature for 3 days. The solution obtained is then evaporated to dryness and the residue recrystallized from methanol. There is obtained 1.0 g. of 1-(N-methyl-β-D-ribofuranuronamidosyl)-imidazole-4,5-dicarboxamide, having a melting point of 214°–215° C. (decomposition).

The same product is obtained in an analogous manner by reacting ethyl 1-desoxy-1-(4,5-dicarbamoylimidazol-1-yl)-β-D-ribofuranuronate with methylamine.

1-(N-ethyl-β-D-ribofuranuronamidosyl)-imidazole-4,5-dicarboxamide, melting point 206°–207° C. (decomposition), is manufactured in an analogous manner by reacting ethyl or methyl 1-desoxy-1-(4,5-dicarbamoylimidazol-1-yl)-β-D-ribofuranuronate with ethylamine.

N,N'-Diethyl-1-(N-ethyl-β-D-ribofuranuronamidosyl)-imidazole-4,5-dicarboxamide (melting point 189°–190° C. from acetonitrile) is manufactured in an analogous manner by reacting methyl 1-desoxy-1-[4,5-(ethylcarbamoyl)imidazol-1-yl]-β-D-ribofuranuronate with ethylamine.

EXAMPLE 10

Preparation of
1-(N-allyl-β-D-ribofuranuronamidosyl)-imidazole-4,5-dicarboxamide 3.7 G. of methyl 1-desoxy-1-(4,5-dicarbamoylimidazol-1-yl)-β-D-ribofuranuronate and 35 ml. of allylamine are boiled at reflux for 18 hours in 500 ml. of methanol. The solution is then evaporated to dryness and the residue recrystallized from ethanol. There are obtained 2.3 g. of 1-(N-allyl-β-D-ribofuranuronamidosyl)-imidazole-4,5-di-carboxamide, having a melting point of 212°–213° C. (decomposition).

EXAMPLE 11

Preparation of ethyl 1-[4(or 5)-carbamoyl-5(or 4)-(nitrocarbamoyl)imidazol-1-yl]-1-desoxy-2,3-di-O-nitro-β-D-ribofuranuronate 2.3 G. of ethyl 1-desoxy-1-(4,5-dicarbamoylimidazol-1-yl)-β-D-ribofuranuronate are dissolved at −40° C. in 30 ml. of fuming nitric acid (D = 1.50). There is added dropwise thereto a mixture, pre-cooled to −20° C., of 10 ml. of oleum and 10 ml. of nitromethane in such a manner that the temperature does not exceed −30° C. The mixture is stirred at −30° to −25° C. for 45 minutes and then added dropwise with vigorous stirring to 1 liter of an ice-water mixture. The separated product is filtered off, washed with cold water and dried over potassium hydroxide in a desiccator. After recrystallization from isopropanol, there are obtained 2.9 g. of ethyl 1-[4(or 5)-carbamoyl-5(or 4)-(nitrocarbamoyl)-imidazol-1-yl]-1-desoxy-2,3-di-O-nitro-β-D-ribofuranuronate, having a melting point of 117°–118° C.

EXAMPLE 12

The following compounds are manufactured by nitration in an analogous manner to that described in Example 11:

Dimethyl 1-(2,3,5-tri-O-nitro-β-D-ribofuranosyl)-imidazole-4,5-dicarboxylate, $[\alpha]_D^{25} = +52.5°(c=1.00$ in chloroform);

1-(2,3,5-tri-O-nitro-β-D-ribofuranosyl)-imidazole-4,5-dicarboxamide, having a melting point of 170° C. (decomposition);

N,N'-dimethyl-N,N'-dinitro-1-(2,3,5-tri-O-nitro-β-D-ribofuranosyl)-imidazole-4,5-dicarboxamide, $[\alpha]_D^{25} = +30.3°(c=1.00$ in chloroform);

methyl 1-[4(or 5)-carbamoyl-5(or 4)-(nitrocarbamoyl)-imidazol-1-yl]-1-desoxy-2,3-di-O-nitro-β-D-ribofuranuronate, having a melting point of 149° C. (decomposition);

1-(N-methyl-2,3-di-O-nitro-β-D-ribofuranuronamidosyl)-N$^4$(or N$^5$)-nitroimidazole-4,5-dicarboxamide, having a melting point of 177° C. (decomposition);

1-(N-ethyl-2,3-di-O-nitro-β-D-ribofuranuronamidosyl)-N$^4$(or N$^5$)-nitroimidazole-4,5- dicarboxamide, having a melting point of 167°–168° C. (decomposition).

EXAMPLE 13

Preparation of N,N'-dimethyl-1-(2,3,5-tri-O-nitro-β-D-ribofuranosyl)-imidazole-4,5-dicarboxamide A solution of 4.6 g. of N,N'-dimethyl-N,N'-dinitro-1-(2,3,5-tri-O-nitro-β-D-ribofuranosyl)-imidazole-4,5-dicarboxamide in 200 ml. of methanol is treated with 3 ml. of 40% methylamine and the mixture left to stand at room temperature for 30 minutes. The mixture is then evaporated to dryness and the residue chromatographed over silica gel with a mixture of hexane and ethyl acetate. After recrystallization from isopropyl ether, there are obtained 1.9 g. of N,N'-dimethyl-1-(2,3,5-tri-O-nitro-β-D-ribofuranosyl)-imidazole-4,5-dicarboxamide, having a melting point of 149° C. (decomposition).

EXAMPLE 14

The following compounds are manufactured in an analogous manner to that described in Example 13 by reacting N,N'-dimethyl-N,N'-dinitro-1-(2,3,5-tri-O-nitro-β-D-ribofuranosyl)-imidazole-4,5-dicarboxamide with the corresponding amines:

N,N'-diethyl-1-(2,3,5-tri-O-nitro-β-D-ribofuranosyl)-imidazole-4,5-dicarboxamide, $[\alpha]_D^{25} = +34.4°(c=1.0$ in dimethylsulfoxide);

N,N'-diallyl-1-(2,3,5-tri-O-nitro-β-D-ribofuranosyl)-imidazole-4,5-dicarboxamide, $[\alpha]_D^{25} = +29.3°(c=1.0$ in dimethylsulfoxide);

N,N'-diphenethyl-1-(2,3,5-tri-O-nitro-β-D-ribofuranosyl)-imidazole-4,5-dicarboxamide, having a melting point of 97°–98° C.;

N,N'-dipropyl-1-(2,3,5-tri-O-nitro-β-D-ribofuranosyl)-imidazole-4,5-dicarboxamide, $[\alpha]_D^{25} = +28.6°(c=0.5$ in dimethylsulfoxide).

EXAMPLE 15

Preparation of 1-(2,3-di-O-nitro-β-D-ribofuranuronamidosyl)-imidazole-4,5-dicarboxamide 2.1 G. of 1-(β-D-ribofuranuronamidosyl)-imidazole-4,5-dicarboxamide are dissolved at a temperature not exceeding −40° C. in 20 ml. of fuming nitric acid. The mixture is subsequently left to warm up to −10° C. and it is held at this temperature for 30 minutes.

The mixture is then poured on to ice, extracted with ethyl acetate, the organic phase washed neutral with 10% potassium bicarbonate solution, dried over magnesium sulfate and concentrated. Recrystallization of the residue from dioxane gives 1.58 g. of 1-(2,3-di-O-nitro-β-D-ribofuranuronamidosyl)-imidazole-4,5-dicarboxamide, having a melting point greater than 183° C. (decomposition).

EXAMPLE 16

Preparation of N,N'-diethyl-1-(N-ethyl-2,3-di-O-nitro-β-D-ribofuranuronamidosyl)-imidazole-4,5-dicarboxamide 5 G. of N,N'-diethyl-1-(N-ethyl-β-D-ribofuranuronamidosyl)-imidazole-4,5-dicarboxamide are dissolved at a temperature not exceeding −30° C. in 55 ml. of fuming nitric acid. To this solution is added a mixture, pre-cooled to −20° C., of 27.5 ml. of nitromethane and 27.5 ml. of oleum and the resulting mixture is then stirred at −15° C. for 4 hours.

The mixture is then poured on to ice, the crystallized-out product filtered off under suction and dried over potassium hydroxide under a high vacuum, there being obtained 8.2 g. of crude nitration product.

The foregoing crude nitration product is dissolved in 20 ml. of tetrahydrofuran, the solution treated with ethylamine in tetrahydrofuran and stirred for 2 hours. The mixture is evaporated in a vacuum and the residue chromatographed over silica gel, there being obtained pure N,N'-diethyl-1-(N-ethyl-2,3-di-O-nitro-β-D-ribofuranuronamidosyl)-imidazole-4,5-dicarboxamide, having a melting point of 106°–109° C.

The following Examples illustrate typical pharmaceutical preparations provided by the present invention:

EXAMPLE A

Capsules containing the following ingredients are produced:

| | |
|---|---|
| N,N'-dimethyl-1-(2,3,5-tri-O-nitro-β-D-ribofuranosyl)-imidazole-4,5-dicarboxamide | 250.0 mg. |
| Lactose | 155.0 mg. |
| Maize Starch | 30.0 mg. |
| Talc | 15.0 mg. |
| | 450.0 mg. |

N,N'-dimethyl-1-(2,3,5-tri-O-nitro-β-D-ribofuranosyl)-imidazole-4,5-dicarboxamide is homogeneously mixed with the lactose and the maize starch, passed through a sieve and, after admixture with the talc, filled into gelatin capsules.

Capsule fill weight: 450 mg.

N,N'-dimethyl-1-(2,3,5-tri-O-nitro-β-D-ribofuranosyl)-imidazole-4,5-dicarboxamide content: 250 mg.

EXAMPLE B

Tablets containing the following ingredients are produced:

| | |
|---|---|
| N,N'-dimethyl-1-(2,3,5-tri-O-nitro-β-D-ribofuranosyl)-imidazole-4,5-dicarboxamide | 250.0 mg. |
| Lactose | 100.0 mg. |
| Maize Starch | 85.0 mg. |
| Ethyl cellulose | 10.0 mg. |
| Talc | 4.5 mg. |
| Magnesium Stearate | 0.5 mg. |
| | 450.0 mg. |

N,N'-dimethyl-1-(2,3,5-tri-O-nitro-β-D-ribofuranosyl)-imidazole-4,5-dicarboxamide is mixed with the lactose and the maize starch and granulated with a solution of the ethyl cellulose in 40 ml. of methylene chloride. The granulate is dried at 40° C., mixed with the talc and magnesium stearate and pressed to tablets.

Weight of one tablet: 450 mg.

N,N'-dimethyl-1-(2,3,5-tri-O-nitro-β-D-ribofuranosyl)-imidazole-4,5-dicarboxamide content of one tablet: 250 mg.

We claim:

1. A compound of the formula

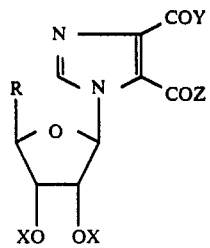

wherein R, X, Y and Z have one of the meanings set forth hereinafter under (1)-(5):

(1) R is —CH$_2$OH;

X is H, and

Y and Z are —C$_{1-4}$-alkoxy, —NH(C$_{1-7}$-alkyl), —NH(C$_{2-4}$-alkenyl), —NH(C$_{3-6}$-cycloalkyl) or —NH-phenyl-(lower alkyl); or (2) R is —CH$_2$ONO$_2$;

X is —NO$_2$; and

Y and Z are —C$_{1-4}$-alkoxy, —NH$_2$, —NH(C$_{1-7}$-alkyl), —NH(C$_{2-4}$-alkenyl), —NH-phenyl-(lower alkyl) or —N(NO$_2$)(C$_{1-7}$-alkyl); or (3) R is —COO(C$_{1-4}$-alkyl), —CONH$_2$, —CONH(C$_{1-4}$-alkyl), —CONH(C$_{2-4}$-alkenyl); —CONH(C$_{3-6}$-cycloalkyl) or —CO—Het wherein Het is a 5-membered or 6-membered heterocyclic ring which may contain, in addition to the nitrogen atom via which it is bound with the carbonyl group, the hetero atom nitrogen, oxygen or sulfur;

X is H; and

Y and Z are —NH$_2$ or —NH(C$_{1-7}$-alkyl); or (4) R is —COO(C$_{1-4}$-alkyl);

X is —NO$_2$; and one of Y and Z is —NH$_2$ and the other is —NHNO$_2$; or (5) R is —CONH$_2$, —CONH(C$_{1-4}$-alkyl) or —CONH(C$_{5-6}$-cycloalkyl);

X is —NO$_2$; and both of Y and Z are —NH$_2$, —NH(C$_{1-7}$-alkyl) or —N(NO$_2$)(C$_{1-7}$-alkyl) or one of Y and Z is —NH$_2$ and the other is —NHNO$_2$.

2. A compound of the formula

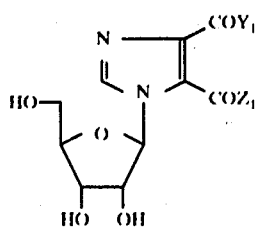

wherein Y$_1$ and Z$_1$ are —C$_{1-4}$-alkoxy, —NH(C$_{1-7}$-alkyl), —NH(C$_{2-4}$-alkenyl), —NH(C$_{1-6}$-cycloalkyl) or —NH-phenyl-(lower alkyl).

3. A compound of the formula

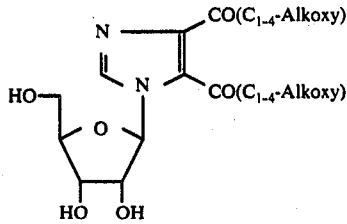

4. A compound of the formula

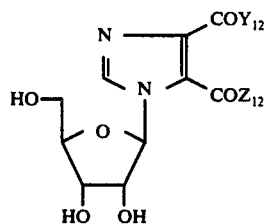

wherein Y$_{12}$ and Z$_{12}$ are —NH(C$_{1-7}$-alkyl), —NH(C$_{2-4}$-alkenyl), —NH(C$_{3-6}$-cycloalkyl) or —NH-phenyl-(lower alkyl).

5. A compound of the formula

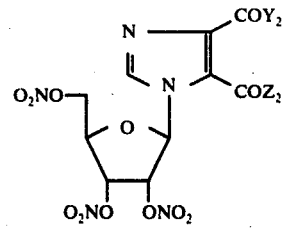

wherein Y$_2$ and Z$_2$ are —C$_{1-4}$-alkoxy, —NH$_2$, —NH(C$_{1-7}$-alkyl), —NH(C$_{2-4}$-alkenyl), —NH-phenyl-(lower alkyl) or —N(NO$_2$)(C$_{1-7}$-alkyl).

6. A compound of the formula

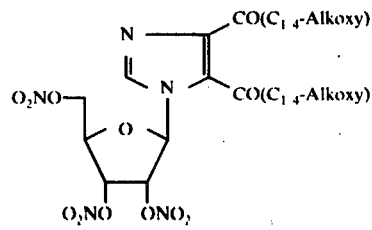

7. A compound of the formula

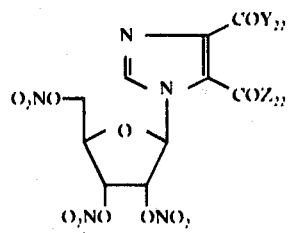

wherein Y$_{22}$ and Z$_{22}$ are —NH$_2$ or —N(NO$_2$)(C$_{1-7}$-alkyl).

8. A compound of the formula

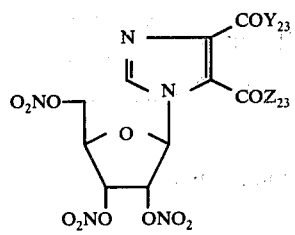

wherein $Y_{23}$ and $Z_{23}$ are —NH($C_{1-7}$-alkyl), —NH($C_{2-4}$-alkenyl) or —NH-phenyl-(lower alkyl).

9. A compound of the formula

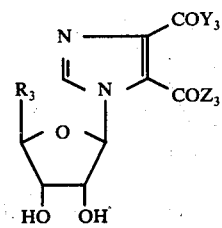

wherein $R_3$ is —COO($C_{1-4}$-alkyl), —CONH$_2$, —CONH($C_{1-4}$-alkyl), —CONH($C_{2-4}$-alkenyl), —CONH($C_{3-6}$-cycloalkyl) or —CO—Het wherein Het is a 5-membered or 6-membered heterocyclic ring which may contain, in addition to the nitrogen atom via which it is bound with the carbonyl group, the hetero atom nitrogen, oxygen or sulfur, and $Y_3$ and $Z_3$ are —NH$_2$ or —NH($C_{1-7}$-alkyl).

10. A compound of the formula

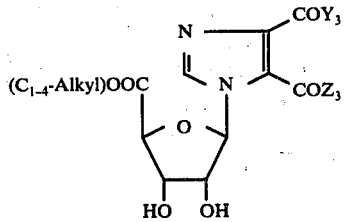

wherein $Y_3$ and $Z_3$ are —NH$_2$ or —NH($C_{1-7}$-alkyl).

11. A compound of the formula

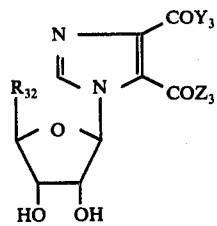

wherein $R_{32}$ is —CONH$_2$, —CONH($C_{1-4}$-alkyl), —CONH($C_{2-4}$-alkenyl), —CONH($C_{3-6}$-cycloalkyl) or —CO—Het wherein Het is a 5-membered or 6-membered heterocyclic ring which may contain, in addition to the nitrogen atom via which it is bound with the carbonyl group, the hetero atom nitrogen, oxygen or sulfur, and $Y_3$ and $Z_3$ are —NH$_2$ or —NH($C_{1-7}$-alkyl).

12. A compound of the formula

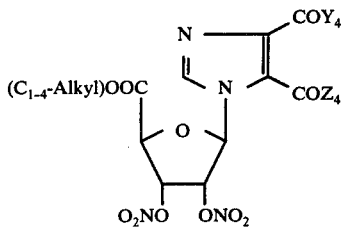

wherein one of $Y_4$ and $Z_4$ is —NH$_2$ and the other is —NHNO$_2$.

13. A compound of the formula

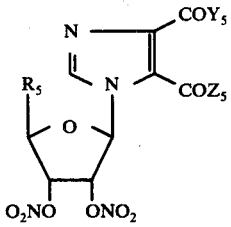

wherein $R_5$ is —CONH$_2$, —CONH($C_{1-4}$-alkyl) or —CONH($C_{5-6}$—cycloalkyl) and both of $Y_5$ and $Z_5$ are —NH$_2$, —NH($C_{1-7}$-alkyl) or —N(NO$_2$)($C_{1-7}$-alkyl) or one of $Y_5$ and $Z_5$ is —NH$_2$ and the other is —NHNO$_2$.

14. A compound of the formula

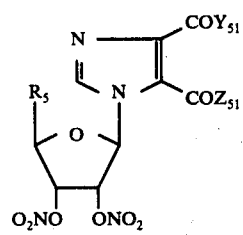

Wherein $R_5$ is —CONH$_2$, —CONH($C_{1-4}$-alkyl) or —CONH($C_{5-6}$-cycloalkyl) and both of $Y_{51}$ and $Z_{51}$ are —NH$_2$ or —N(NO$_2$)($C_{1-7}$-alkyl) or one of $Y_{51}$ and $Z_{51}$ is —NH$_2$ and the other is —NHNO$_2$.

15. A compound of the formula

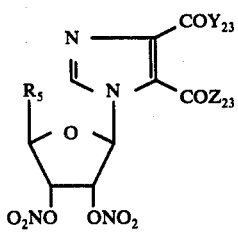

wherein $R_5$ is —CONH$_2$, —CONH($C_{1-4}$-alkyl) or —CONH($C_{5-6}$-cycloalkyl) and $Y_{23}$ and $Z_{23}$ are —NH(-$C_{1-7}$-alkyl), —NH($C_{2-4}$-alkenyl) or —NH-Phenyl-(lower alkyl).

16. A compound in accordance with claim 5, N,N'-dimethyl-1-(2,3,5-tri-O-nitro-β-D-ribofuranosyl)-imidazole-4,5-dicarboxamide.

17. A compound in accordance with claim 13, 1-(2,3-Di-O-nitro-β-D-ribofuranuronamidosyl)-imidazole-4,5-dicarboxamide.

* * * * *